(12) United States Patent
Bauer et al.

(10) Patent No.: US 7,250,540 B2
(45) Date of Patent: Jul. 31, 2007

(54) PROCESS FOR MANUFACTURING FLUOROOLEFINS

(75) Inventors: Gerald L. Bauer, Hudson, WI (US); Jeffrey D. Weigelt, Woodbury, MN (US); Klaus Hintzer, Kastl (DE); Gernot Loehr, Burgkirchen (DE); Werner Schwertfeger, Altoetting (DE); Arthur A. Ponelis, Pretoria (ZA)

(73) Assignee: 3M Innovative Properties Company, St. Paul, MN (US)

( * ) Notice: Subject to any disclaimer, the term of this patent is extended or adjusted under 35 U.S.C. 154(b) by 213 days.

(21) Appl. No.: 11/170,385

(22) Filed: Jun. 29, 2005

(65) Prior Publication Data

US 2005/0240067 A1 Oct. 27, 2005

Related U.S. Application Data

(62) Division of application No. 10/320,796, filed on Dec. 16, 2002, now Pat. No. 6,919,015.

(51) Int. Cl.
C07C 17/06 (2006.01)
C07C 17/013 (2006.01)

(52) U.S. Cl. ............ 570/153; 570/155; 570/140; 570/156

(58) Field of Classification Search ............ 570/153, 570/155, 140, 156
See application file for complete search history.

(56) References Cited

U.S. PATENT DOCUMENTS

| | | | |
|---|---|---|---|
| 2,519,983 A | 8/1950 | Simons | |
| 2,551,573 A | 5/1951 | Downing et al. | |
| 2,567,011 A | 9/1951 | Diesslin et al. | |
| 3,081,245 A | 3/1963 | Farlow | |
| 3,662,009 A | 5/1972 | Hutchinson | |
| 3,753,976 A | 8/1973 | Grass, Jr. et al. | |
| 3,816,552 A | 6/1974 | Hartwimmer | |
| 3,832,411 A | 8/1974 | Arkles et al. | |
| 3,904,501 A | 9/1975 | Lagow et al. | |
| 3,957,596 A | 5/1976 | Seto | |
| 4,076,760 A | 2/1978 | Hartwimmer | |
| 4,139,447 A | 2/1979 | Faron et al. | |
| 4,203,821 A | 5/1980 | Cramer et al. | |
| 4,406,768 A | 9/1983 | King | |
| 4,898,645 A | 2/1990 | Voigt et al. | |
| 4,933,060 A | 6/1990 | Prohaska et al. | |
| 4,950,370 A | 8/1990 | Tarancon | |
| 4,973,773 A | 11/1990 | Malone | |
| 5,026,464 A | 6/1991 | Mizuno et al. | |
| 5,110,996 A | 5/1992 | Edwards | |
| 5,207,999 A | 5/1993 | Burk et al. | |
| 5,322,597 A | 6/1994 | Childs et al. | |
| 5,387,232 A | 2/1995 | Minday et al. | |
| 5,399,832 A | 3/1995 | Tanisaki et al. | |
| 5,461,117 A | 10/1995 | Bierschenk et al. | |
| 5,488,142 A | 1/1996 | Fall et al. | |
| 5,578,278 A | 11/1996 | Fall et al. | |
| 5,611,896 A | 3/1997 | Swanepoel et al. | |
| 5,633,414 A | 5/1997 | Webster | |
| 5,684,218 A | 11/1997 | Webster | |
| 5,744,657 A | 4/1998 | Webster | |
| 5,759,237 A | 6/1998 | Li et al. | |
| 5,814,127 A | 9/1998 | Li | |
| 5,858,065 A | 1/1999 | Li | |
| 5,919,285 A | 7/1999 | Li et al. | |
| 6,267,865 B1 | 7/2001 | Polson et al. | |
| 6,288,291 B1 | 9/2001 | Van Der Westhuizen et al. | |
| 6,624,337 B1 | 9/2003 | Manzer et al. | |
| 6,919,015 B2 | 7/2005 | Bauer et al. | |

FOREIGN PATENT DOCUMENTS

| | | |
|---|---|---|
| EP | 0 282 827 A2 | 9/1988 |
| EP | 0 455 399 A2 | 11/1991 |
| EP | 0 647 607 B1 | 4/1995 |
| EP | 0 515 975 B1 | 10/1996 |
| EP | 0 809 621 B1 | 12/1997 |
| GB | 766324 | 1/1957 |
| GB | 1 516 648 | 7/1978 |
| JP | 2-30785 | 4/1988 |
| SU | 1666581 A | 7/1988 |
| WO | WO 95/21126 | 8/1995 |
| WO | WO 96/25378 | 8/1996 |
| WO | WO 96/30322 | 10/1996 |
| WO | WO 96/30323 | 10/1996 |
| WO | WO 98/50603 | 11/1998 |
| WO | WO 00/71492 A1 | 11/2000 |
| WO | WO 00/75092 A1 | 12/2000 |
| WO | WO 01/00156 A1 | 1/2001 |
| WO | WO 01/58584 A3 | 8/2001 |
| WO | WO 01/58840 A2 | 8/2001 |
| WO | WO 01/58841 A1 | 8/2001 |

OTHER PUBLICATIONS

"Fluorine Reactions in Plasma," the Application of Plasmas to Chem Proc., RF Baddour; RS Timmins, MIT Press Mass., (1967), pp. 157-200.

*Primary Examiner*—Elvis O. Price

(57) ABSTRACT

A process for manufacturing fluoroolefins comprising perfluorinating a starting material comprising at least one carbon-bonded hydrogen by electrochemical fluorination, dissociating this separated effluent in a pyrolysis, quenching and separating the effluent to yield tetrafluoroethylene and/or hexafluoropropylene.

12 Claims, 2 Drawing Sheets

PROCESS FOR MANUFACTURING FLUOROOLEFINS

This application is a Divisional application of prior application Ser. No. 10/320,796 filed Dec. 16, 2002, now U.S. Pat. No. 6,919,015, the disclosure of which is herein incorporated by reference.

FIELD OF INVENTION

This invention relates to a process for manufacturing fluoroolefins.

BACKGROUND OF INVENTION

Tetrafluoroethylene (TFE) and hexafluoropropylene (HFP) are widely used as monomers in the manufacture of plastic and elastomeric fluoropolymers. See, for example, J. Scheirs in *Modern Fluoropolymers*, Wiley, 1996. The worldwide consumption of TFE exceeds $10^5$ tons/year. HFP is used as a comonomer to manufacture thermoplastic and elastomeric fluoropolymers and as starting material for making hexafluoropropene oxide (HFPO). The worldwide consumption is estimated to be 30,000 tons/year.

There are several known methods for manufacturing TFE and HFP. The most common method and almost exclusively used at industrial scale, involves pyrolyzing $CHClF_2$ (R-22). See for example, U.S. Pat. No. 2,551,573. The high temperature (600° C. to 1000° C.) pyrolysis of $CHClF_2$ yields TFE and HFP in high yields. But there are environmental concerns with R-22. This process produces equimolar amounts of aqueous hydrochloric acid and considerable amounts of partially fluorinated and chlorinated compounds, which are difficult to separate from TFE to obtain polymerization grade TFE (U.S. Pat. No. 4,898,645). For the aqueous hydrochloric acid, industrial applications are generally sought that can use the aqueous hydrochloric acid. The fluorinated and other side products have to be incinerated through thermal oxidizers, which is another costly process and produces high amounts of $CO_2$.

U.S. Pat. No. 5,611,896 describes a process where elemental fluorine is reacted with carbon to produce $CF_4$, which is converted to TFE in a plasma torch in the presence of carbon. Unreacted $CF_4$ is fed back to the plasma. Thus, this technology is advantageously "closed-loop" which means emissions to the environment are minimal. But this process is hardly economically viable due to the use of costly elemental fluorine and the high-energy consumption involved.

U.S. Pat. Nos. 5,633,414 and 5,684,218 describe a plasma process, where metal fluorides, particularly $CaF_2$ as a cost efficient fluorine source, are reacted with carbon in a plasma. Thus, the costs for elemental fluorine are avoided. This technology still requires high-energy consumption.

A further method described in the art involves reacting TFE and/or HFP with ethylene and then fluorinating the cyclobutanes by electrochemical fluorination (ECF). This perfluoro-cyclobutane product is then pyrolyzed using conventional pyrolyzing techniques as described for example in EP 455,399 including the references cited therein and WO 00/75092. Any by-products formed in the ECF process are separated off and are not further used in accordance with the teaching of WO 00/75092. Accordingly, substantial waste material is produced with this process, which causes an environmental burden and makes the process economically less attractive. Additionally, the process requires the use of TFE as one of the starting compounds, which creates an additional economical disadvantage as part of the TFE produced is needed to produce further TFE.

U.S. Pat. No. 3,081,245 discloses a process for preparing TFE that comprises feeding a saturated perfluorocarbon to a continuous electric arc, passing the emerging gaseous product through a carbon bed at a temperature of 2700° C. to 2000° C. and quenching the resulting gaseous product mixture to less than 500° C. in less than one second.

EP 371,747 discloses a process for making TFE by heating in the presence of a gas selected from Ar, HF, CO, $CF_4$, and $CO_2$ at a temperature of at least 2000° K. a $C_2$ to $C_{10}$ compound containing fluorine and hydrogen in which the F to H ratio is greater than or equal to 1 and the F to C ratio is greater than or equal to 1. Heating is carried out with a Direct Current (DC) plasma or through radio frequency energy.

Another chlorine-free process for making TFE is disclosed in GB 766 324 by pyrolyzing a fluorocarbon with at least 3 carbons per molecule. Pyrolyzing occurs at a temperature of at least 1500° C. preferably generated in an electric arc. The side products of the pyrolysis are fed back in the pyrolysis furnace after the separation of TFE. The fluorocarbons to be pyrolyzed are obtained from exhaustive fluorination of petroleum fractions using elemental fluorine, which renders the process economically unattractive.

Still another chlorine-free method to make TFE is described in EP 0 647 607. Finely divided fluoropolymers such as PTFE or perfluoro- or highly fluorinated copolymers are pyrolyzed with superheated steam. The source of this feedstock is scrap material that cannot be used, or materials from worn out equipment. This process is an economical management of waste material. Another chlorine-free process to make TFE is described in WO 01/58840-A2. Solid particulate fluorocarbons, particularly PTFE and highly or perfluorinated polymers are subjected to DC plasma to yield TFE. Still another chlorine-free process to make TFE is disclosed in WO 01/58841-A1 where gaseous or liquid fluorocarbons are pyrolyzed via DC plasma. Another chlorine-free process to make TFE is described in WO 01/58584-A2. Gaseous, liquid, and solid perfluorocarbons, particularly perfluoropolymers, are pyrolyzed via inductive heating. These processes cannot replace the standard technology via R-22, because the technology does not produce new C—F-bonds and therefore cannot meet the demand for TFE.

Thus, the need exists for a process to manufacture TFE and/or HFP that is efficient, environmentally friendly, and/or cost efficient.

SUMMARY OF THE INVENTION

We have found a process for manufacturing TFE that may have an efficient yield (overall yield preferably is higher than 90% based on a hydrocarbon feed) and may eliminate a hydrochloric acid waste stream. The process of the present invention may also produce HFP and can thus be used to make both TFE and HFP if desired. The process generally involves less separation efforts to purify TFE, can be designed in a cost efficient manner, and can be designed as a so-called closed-loop in which no or very low amounts of waste material is created. This closed-loop process is environmentally advantageous.

The present invention provides a process for manufacturing tetrafluoroethylene and/or hexafluoropropylene comprising:

(a) perfluorinating a starting material comprising a linear or branched hydrocarbon compound and/or a partially fluorinated linear or branched hydrocarbon compound by electrochemical fluorination (ECF) in an electrochemical cell (ECF cell) in a solution of anhydrous liquid hydrogen fluoride under temperature and pressure conditions sufficient to replace all hydrogens in at least part of the starting material with fluorine, to yield an ECF effluent;

(b) separating said ECF effluent to yield a perfluorinated feed material;

(c) pyrolyzing said perfluorinated feed material to yield a reaction mixture;

(d) quenching said reaction mixture to yield a product mixture; and (e) recovering tetrafluoroethylene and/or hexafluoropropylene from said product mixture.

According to one embodiment, the pyrolysis of step (c) is carried out in the presence of carbon. This allows for the conversion of perfluorinated compounds that have a high F to C ratio such as $CF_4$ and $C_2F_6$. These compounds are typically present in an off-gas stream of the ECF cell and can in accordance with an embodiment of the present invention be separated therefrom and thus pyrolyzed in the presence of carbon. The pyrolysis may proceed with a DC plasma or through inductive heating and is preferably carried out in the presence of carbon. For inductive heating, the pyrolysis may be carried out at a temperature of at least 500° C., generally from 500° C. to 3000° C. (inclusive), typically between 700° C. and 3000° C. (inclusive), or between 900° C. and 1500° C. (inclusive).

Figure 1:
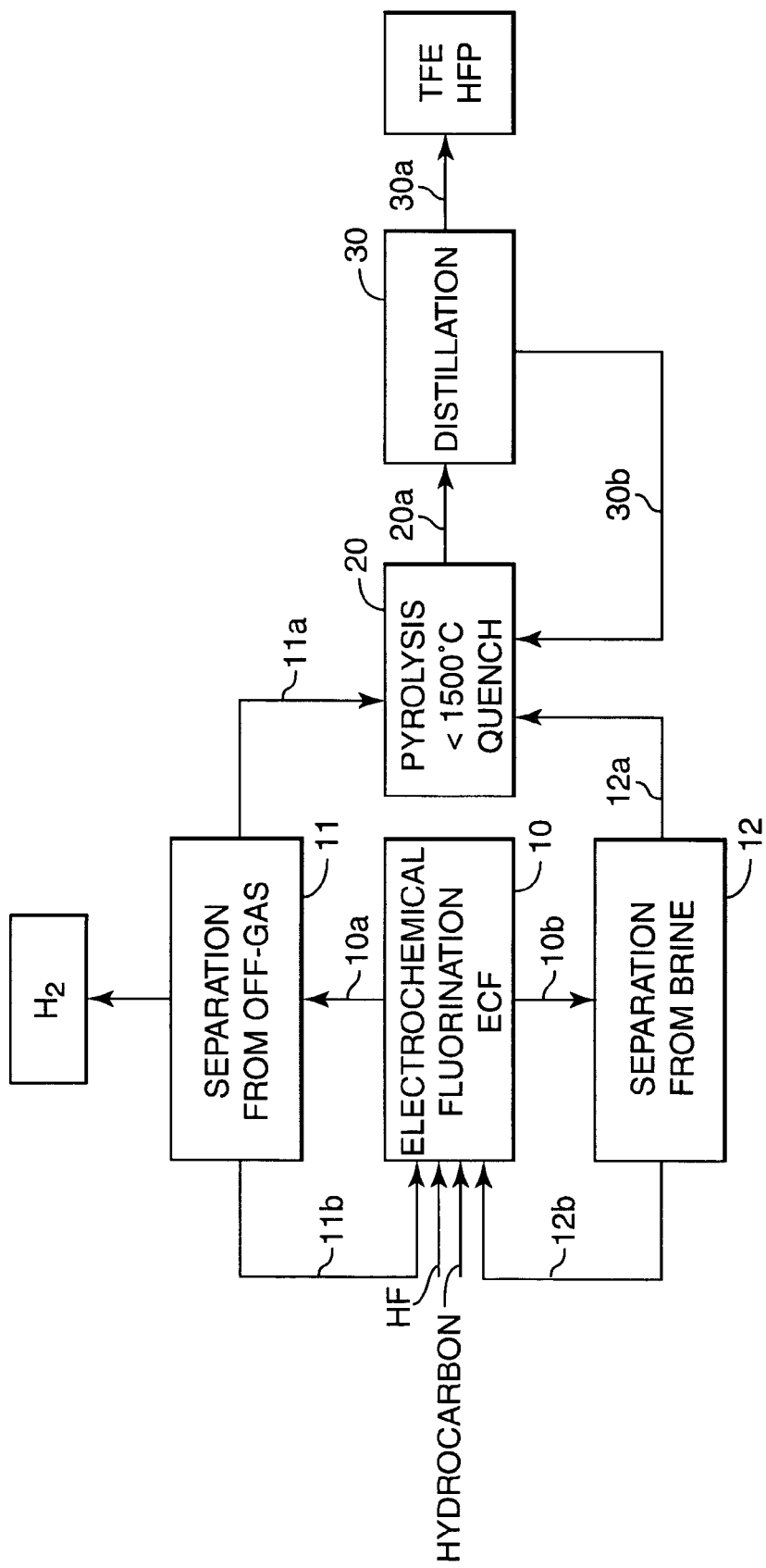
FIG. 1 shows schematically one embodiment of the inventive process as a closed-loop. A hydrocarbon feedstock is electrochemically fluorinated in ECF cell 10. The lower boiling fluorocarbons are separated 11 from the off-gas, mainly hydrogen, stream 10a, and optionally further separated into perfluorinated compounds to be fed in pyrolysis furnace 20, stream 11a, and partially fluorinated compounds to be fed back to ECF cell 10, stream 11b. The higher boiling fluorinated chemical compounds are separated, 12, from ECF effluent 10b or so-called brine of ECF cell 10, stream 10b. These fluorinated compounds are further separated in perfluorinated compounds to be fed as the perfluorinated feed material in pyrolysis furnace 20 and partially fluorinated compounds that are fed back to ECF cell 10, stream 12b.

The perfluorinated compounds of stream 11a and 12a are pyrolyzed at temperatures of 500° C. to 3000° C. in a pyrolysis furnace 20 and quenched. Quenched gases, stream 20a, are subjected to distillation 30 yielding TFE and optionally HFP, and undesired by-products, which are fed back to pyrolysis furnace 20, stream 30b.

Figure 2:
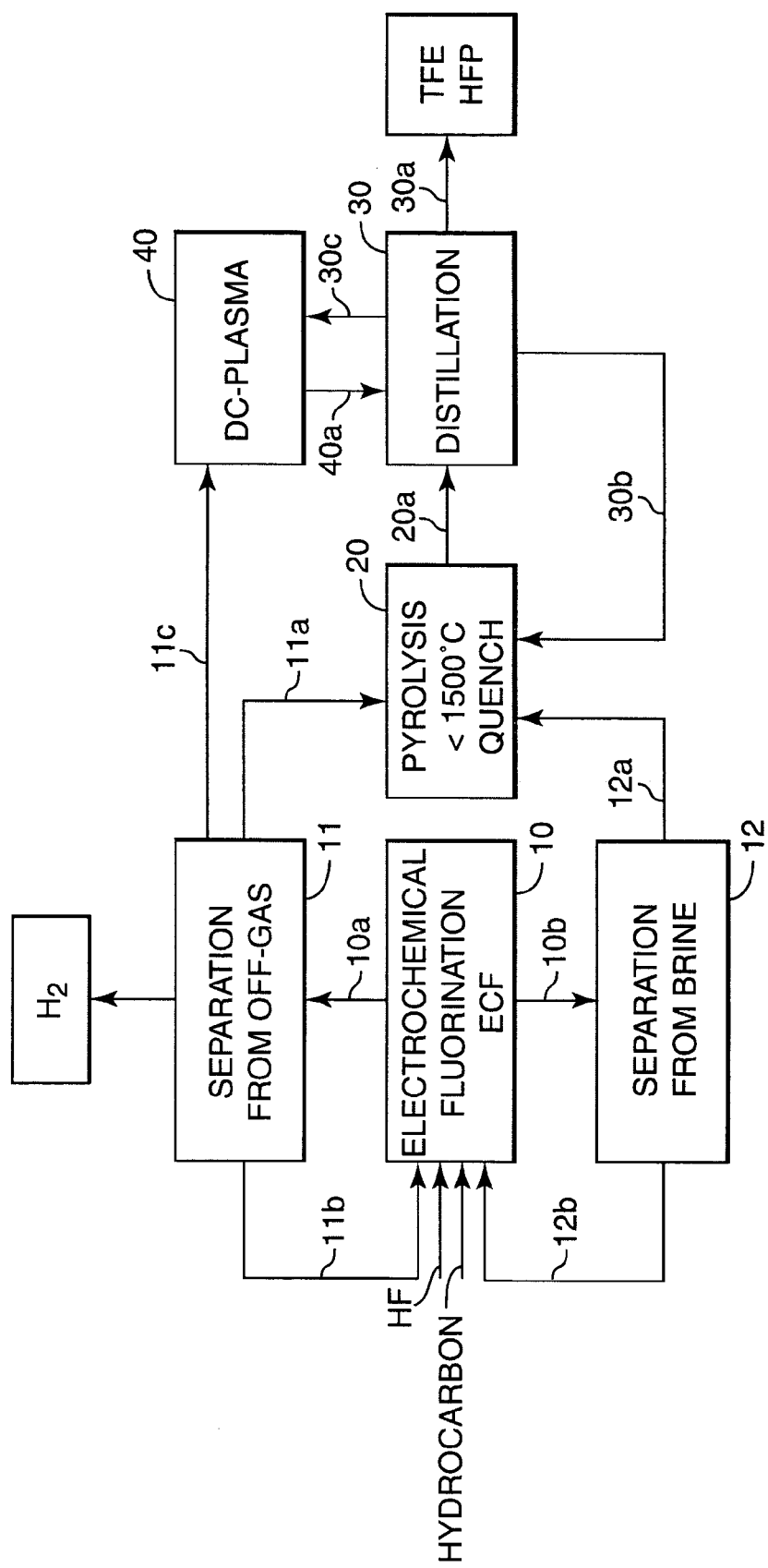

FIG. 2 shows another embodiment of the present invention. The stream 30b of FIG. 1 is now fed into a DC plasma furnace 40, stream 30c. The quenched pyrolyzed gases are fed back to distillation 30, stream 40a, to recover TFE and optionally HFP therefrom. In this embodiment, all or part of the perfluorinated compounds from the off-gas stream 10a of the ECF cell may be fed in DC plasma furnace 40, as carrier gases (stream 11c).

These figures are not to scale and are intended to be merely illustrative and nonlimiting.

DETAILED DESCRIPTION OF ILLUSTRATIVE EMBODIMENTS

The present invention provides a process for manufacturing tetrafluoroethylene and/or hexafluoropropylene. The process involves perfluorinating a starting material using electrochemical fluorination and then feeding the perfluorinated material into a pyrolysis furnace to yield TFE and optionally HFP.

The process of the present invention is preferably designed as a closed-loop process where all perfluorinated compounds can be converted into fluoroolefins and all undesired byproducts (e.g., C—H containing/partially fluorinated materials) can be recycled until completion. This reduces the process cost and fluorinated compounds in waste streams. Thus, the process of the present invention is environmentally responsible. A variety of hydrocarbons (linear, branched, saturated, unsaturated) can be fed into the ECF cell. The perfluorinated ECF effluent is fed into the pyrolysis and the partially fluorinated materials are fed back to the ECF cell. For the purposes of this invention, partially fluorinated materials that are fed back to the ECF cell are generally referred to as starting materials. In the pyrolysis, desired TFE and/or HFP is produced. Any perfluorinated waste products can be recycled and again be subjected to pyrolysis. The pyrolysis is preferably carried out in the presence of carbon. Inductive heating is advantageously used but also DC plasma can be used. When inductive heating is used, the pyrolysis can proceed at a temperature of at least 500° C. and not more than 3000° C. Any partially fluorinated compounds in the waste streams can be re-fed into the ECF cell.

Advantageously, the present invention requires less separation efforts than processes known in the art especially during the separation and purification of TFE. This reduces the costs involved. The capital and energy costs are less because simple distillation is involved (fewer columns) versus R-22 pyrolysis. In addition, the process of the present invention may be economically feasible even at a smaller volume scale (e.g., 1000 tons/year) than the processes known in the art, and thus may require less capital expenditure. TFE cannot be efficiently transported because of its instability. Therefore, TFE is typically converted to a polymer or further processed prior to transport. Thus, it is advantageous to be able to produce TFE at the site where the end polymer is produced. Because the process of the present invention is economically feasible at low volume production, the TFE can be readily produced at the site where the end polymer is made.

"Fluorinated" refers to chemical compounds having at least one carbon-bonded hydrogen replaced by a fluorine, and specifically includes perfluorinated compounds and partially fluorinated compounds, i.e., compounds that have C—F and C—H bonds in the molecule.

"Perfluorinated" compounds refers to chemical compounds where essentially all carbon-bonded hydrogens have been replaced by fluorines, although typically some residual hydride will be present in a perfluorinated composition; e.g., preferably less than 2 weight % perfluorinated product.

One embodiment of the process of the present invention is set forth in FIG. 1. In FIG. 1, HF and starting material are fed into ECF cell 10. ECF effluent stream 10b is then fed to separation process 12 and off-gas from the ECF cell, stream 10a, is fed to a membrane process 11. Membrane process 11 separates off-gas stream 10a, partially fluorinated compounds 11b, and perfluorinated compounds 11a. Partially fluorinated compounds are returned to ECF cell 10 for further processing. Off-gas ($H_2$) may be vented or used for energy production. ECF effluent stream 10b is separated 12 and desired perfluorinated compound stream 12a and perfluorinated compounds stream 11a are fed to pyrolysis furnace 20. After pyrolysis, product mixture stream 20a is then fed into separation process 30, which typically is a simple distillation. The desired products TFE and/or HFP are separated out (30a). Undesirable fluorine-containing products stream 30b are returned to pyrolysis furnace 20 for further processing.

In FIG. 2, perfluorinated compounds, stream 11c, from off-gas stream 10a and the perfluorinated compounds from distillation 30 (stream 30c) are subjected to DC plasma 40. The reaction mixture of DC plasma 40 is quenched and then fed into separation process 30 (stream 40a). Off-gas perfluorinated compounds stream 11c may be fed into DC plasma 40-in which case stream 11a will not be present or only part thereof may be fed into DC plasma 40 such that both streams 11a and 11c co-exist. Likewise, only stream 40a may be used or alternatively co-exist with stream 30b.

Starting Materials

A variety of materials can be used as the starting materials for ECF. The starting material can be a gas, a liquid, or a mixture thereof. The starting material generally comprises linear or branched hydrocarbon compounds, partially fluorinated linear or branched hydrocarbon compounds or mixtures thereof. The linear or branched hydrocarbon compound generally consists of carbon and hydrogen but hydrocarbon compounds having one or more substituents such as hydroxy, amino groups, carboxy groups, sulphonic acid groups and amide groups are within the scope of the term 'hydrocarbon compound' as used in this invention. Preferably, however the starting material will be substantially free of chlorine, bromine, or iodine containing materials as these create undesirable waste material. "Substantially free" means that the starting material is either free of or contains a material in amount of not more than 1 or 2% by weight relative to the total weight of starting material. The starting material may contain cyclic compounds, such as cyclic hydrocarbons in admixture with the linear or branched (partially fluorinated) hydrocarbon compounds. The process provides for the use of mixtures of compounds as the starting material and these mixtures may be complex in that they contain a large variety of different compounds.

Preferably, the starting material comprises a straight or branched alkane that is entirely hydrocarbon (e.g., a straight chain alkane, $C_nH_{2n+2}$, wherein n is from about 3 to 25, preferably from about 4 to 8 or 10, and more preferably n is 4 to 6), or, a partially fluorinated analog thereof (e.g., $C_nH_xX_y$, wherein X is fluorine, and wherein x is at least 1 and x+y=2n+2). The hydrocarbon compound may comprise saturated and unsaturated compounds including olefins and aromatic compounds such as benzene, toluene, or xylene. Examples of especially preferred starting materials include butane, pentane, hexane, heptane, and octane. Examples of preferred readily available starting materials include methane and hydrocarbons up to $C_{10}$ and mixtures thereof, and mixtures of hydrocarbons with olefins (e.g., isobutylene, etc.). A particular hydrocarbon starting material includes crude oil and petroleum fractions, so-called distillation cuts originating from refining of crude oil and from making olefins such as ethylene and propylene. Preferably, the boiling point of these petroleum fractions is not more than 200° C., and more preferably not more than 150° C. or 100° C.

To keep the overall ECF cell pressure low, preferably the gaseous starting material has a boiling point of at least −50° C. and is easy to liquefy, e.g., propane (b.p. −42° C.), propene (b.p. −47° C.), butane (b.p. 0° C.), butene (b.p. −6° C.), isobutylene (b.p. −7° C.). To ensure a fast and complete fluorination, the liquid starting materials are preferably compounds having 10 carbon atoms or less; otherwise the fluorination proceeds slowly and extensive branching and fragmentation can occur, which makes the separation step more difficult. Mixtures of hydrocarbons and their isomers and olefins may be added to the ECF cell as starting materials. Significantly, for the purposes of this invention, partially fluorinated materials fed back to the ECF cell are included in the term starting material.

Electrochemical Fluorination

Generally any electrochemical fluorination process can be used to perfluorinate the starting material. For example, the Simons electrochemical fluorination process, the interrupted current process (see WO Publication 98/50603), the bipolar flow cell (see U.S. Pat. No. 5,322,597), the SOLUTIA EHD process, and the like, may be used.

The Simons electrochemical fluorination (Simons ECF) process was commercialized initially in the 1950s by Minnesota Mining and Manufacturing Company. This ECF process comprises passing a direct electric current through an electrolyte, (i.e., a mixture of fluorinatable organic starting compound, liquid anhydrous hydrogen fluoride, and perhaps a conductivity additive), to produce the desired fluorinated compound or fluorochemical. Simons ECF cells typically utilize a monopolar electrode assembly, i.e., electrodes connected in parallel through electrode posts to a source of direct current at a low voltage (e.g., four to eight volts). Simons ECF cells are generally undivided, single-compartment cells, i.e., the cells typically do not contain anode or cathode compartments separated by a membrane or diaphragm. The Simons ECF process is disclosed in U.S. Pat. No. 2,519,983 (Simons) and is also described in some detail by J. Burdon and J. C. Tatlow in *Advances in Fluorine Chemistry* (M. Stacey, J. C. Tatlow, and A. G. Sharpe, editors) Volume 1, pages 129-37, Buttersworths Scientific Publications, London (1960); by W. V. Childs, L. Christensen, F. W. Klink, and C. F. Kolpin in *Organic Electrochemistry* (H. Lund and M. M. Baizer, editors), Third Edition, pages 1103-12, Marcel Dekker, Inc., New York (1991); by A. J. Rudge in *Industrial Electrochemical Processes* (A. T. Kuhn, editor), pages 71-75, Marcel Dekker, Inc., New York (1967); and by F. G. Drakesmith, *Topics Curr. Chem.*, 193, 197, (1997).

Simons ECF can be carried out essentially as follows. A starting material and an optional conductivity additive are dispersed or dissolved in anhydrous hydrogen fluoride to form an electrolytic "reaction solution." One or more anodes and one or more cathodes are placed in the reaction solution and an electric potential (voltage) is established between the anode(s) and cathode(s), causing electric current to flow between the cathode and anode, through the reaction solution, and resulting in an oxidation reaction (primarily fluorination, i.e., replacement of one or more carbon-bonded hydrogens with carbon-bonded fluorines) at the anode, and a reduction reaction (primarily hydrogen evolution) at the cathode. As used herein, "electric current" refers to electric current in the conventional meaning of the phrase, the flow of electrons, and also refers to the flow of positively or negatively charged chemical species (ions). The Simons ECF process is well known, and the subject of numerous technical publications. An early patent describing the Simons ECF process is U.S. Pat. No. 2,519,983 (Simons), which contains a drawing of a Simons cell and its appurtenances. A description and photograph of laboratory and pilot plant-scale electrochemical fluorination cells suitable for practicing the Simons ECF process appear at pages 416-418 of Vol. 1 of "Fluorine Chemistry," edited by J. H. Simons, published in 1950 by Academic Press, Inc., New York. U.S. Pat. No. 5,322,597 (Childs et al.) and U.S. Pat. No. 5,387,323 (Minday et al.) each refer to the Simons ECF process and Simons ECF cell.

Generally the Simons ECF process is practiced with a constant current passed through the electrolyte; i.e., a constant voltage and constant current flow. See for example W. V. Childs, et al., *Anodic Fluorination* in Organic Electrochemistry, H. Lund and M. Baizer eds., Marcel Dekker Inc., New York, 1991. The current passing through the electrolyte causes one or more of the hydrogens of the starting material to be to be replaced by fluorine.

Various modifications and/or improvements have been introduced to the Simons ECF process since the 1950s including, but not limited to, those described in U.S. Pat. No. 3,753,976 (Voss et al.); U.S. Pat. No. 3,957,596 (Seto); U.S. Pat. No. 4,203,821 (Cramer et al.); U.S. Pat. No. 4,406,768 (King); Japanese Patent Application No. 2-30785 (Tokuyama Soda K K); SU 1,666,581 (Gribel et al.); U.S. Pat. No. 4,139,447 (Faron et al.); and U.S. Pat. No. 4,950,370 (Tarancon).

Another useful electrochemical fluorination cell includes the type generally known in the electrochemical fluorination art as a flow cell. Flow cells comprise a set (one of each), stack, or series of anodes and cathodes, where reaction solution is caused to flow over the surfaces of the anodes and cathodes using forced circulation. These types of flow cells are generally referred to as monopolar flow cells (having a single anode and a single cathode, optionally in the form of more than a single plate, as with a conventional electrochemical fluorination cell), and, bipolar flow cells (having a series of anodes and cathodes).

U.S. Pat. No. 5,322,597 (Childs et al.) incorporated by reference herein more recently describes the practice in a bipolar flow cell of an electrochemical fluorination process comprising passing by forced convection a liquid mixture comprising anhydrous hydrogen fluoride and fluorinatable organic compound at a temperature and a pressure where a substantially continuous liquid phase is maintained between the electrodes of a bipolar electrode stack. The bipolar electrode stack comprises a plurality of substantially parallel, spaced-apart electrodes made of an electrically conductive material, e.g., nickel, which is essentially inert to anhydrous hydrogen fluoride and when used as an anode, is active for electrochemical fluorination. The electrodes of the stack are arranged in either a series or a series-parallel electrical configuration. The bipolar electrode stack has an applied voltage difference that produces a direct current that can cause the production of fluorinated organic compound.

Another example of a bipolar flow cell is the Solutia EHD (electrohydrodimerization) cell. See *J. Electrochem. Soc.*: REVIEWS AND NEWS, D. E. Danly, 131(10), 435C-42C (1984) and *Emerging Opportunities for Electroorganic Processes*, D. E. Danly, pages 132-36, Marcel Dekker, Inc., New York (1984).

In the interrupted current electrochemical fluorination process generally a reaction solution is prepared that comprises hydrogen fluoride and a starting material. The hydrogen fluoride is preferably anhydrous hydrogen fluoride, meaning that it contains at most only a minor amount of water, e.g., less than about 1 weight percent (wt %) water, preferably less than about 0.1 weight percent water. The reaction solution within the ECF cell includes an electrolyte phase comprising HF and an amount of starting material dissolved therein. In general, the starting material is preferably to some degree soluble or dispersible in liquid hydrogen fluoride. Gaseous starting materials can be bubbled through the hydrogen fluoride to prepare the reaction solution, or charged to the cell under pressure. Solid or liquid starting materials can be dissolved or dispersed in the hydrogen fluoride. Starting materials that are relatively less soluble in hydrogen fluoride can be introduced to the cell as a solute dissolved in a fluorochemical fluid.

The reaction solution is exposed to reaction conditions (e.g., temperature, pressure, electric voltage, electric current, and power) sufficient to cause fluorination of the starting material. Reaction conditions chosen for a particular fluorination process depend on factors such as the size and construction of the ECF cell, the composition of the reaction solution, the presence or absence of a conductivity additive, flow rate, etc.

The reaction temperature can be any temperature that allows a useful degree of fluorination of the starting material. The temperature may depend on the factors discussed in the preceding paragraph, as well as the solubility of the starting material and the physical state of the starting material or the fluorinated product.

The electricity passed through the reaction solution can be any amount that will result in fluorination of the starting material. The current is preferably insufficient to cause excessive fragmentation of the starting material or to cause the liberation of fluorine gas during fluorination.

The ECF effluent can be separated using conventional techniques such as distillation. The desired perfluorinated compounds are then fed to the pyrolysis. The insufficiently fluorinated compounds are returned to the ECF cell for perfluorination.

The amounts of partially fluorinated materials in the feed to the pyrolysis (i.e., that still contain a C—H bond) preferably is less than 10 weight percent, more preferably less than 5 weight percent, and most preferably less than 2 weight percent.

Membrane Process/Separation

The ECF cell may have one or more membrane systems to capture the off-gas. Typically the off-gas is hydrogen ($H_2$). Some fluorine-containing compounds (i.e., perfluorinated and non-perfluorinated compounds) are typically carried over by the off-gas. A membrane process can be used to capture the partially fluorinated and perfluorinated compounds and then the partially fluorinated compounds can be fed back into the ECF cell. By introducing membrane separation, only $H_2$ is released from the overall process, advantageously resulting in a closed-loop process. The hydrogen gas released may find further use in generating energy for the process or to provide energy elsewhere in a manufacturing plant.

Membranes separate gases by the principle of selective permeation across the membrane wall. For polymeric membranes, the rate of permeation of each gas is determined by its solubility in the membrane material and the rate of diffusion through the molecular free volume in the membrane wall. Gases that exhibit high solubility in the membrane and gases that are small in molecular size, permeate faster than larger, less soluble gases.

The output from the ECF process includes a large volume of hydrogen, perfluorinated product, and partially fluorinated materials. The membrane process separates the hydrogen from the fluorinated species by allowing the smaller, more soluble hydrogen to pass through the membrane while concentrating the fluorinated material (permeate). The desire is to recover greater than 99% of the fluorinated materials at greater than 99.9% purity (<<1% $H_2$).

Suitable membranes are commercially available. One commercially available membrane is the MEDAL™ Gas-separation membrane available from Air Liquide, Houston, Tex. (See also U.S. Pat. Nos. 5,858,065; 5,919,285; 5,814,127; and 5,759,237.)

Alternatively, a cryogenic distillation process may be used to separate the off-gas ($H_2$). In addition, catalytic "cold combustion" of $H_2$ by metals (e.g., platinum) in the presence of $O_2$ can be used.

Pyrolysis

Pyrolysis is defined as subjecting perfluorinated materials obtained from the ECF, streams 11a and 12a, to temperatures above 500° C. thereby heat cracking the perfluorinated materials e.g., in a pyrolysis furnace (e.g., pyrolysis furnace, FIG. 1). The perfluorinated compounds can be fed in the furnace as gases mostly under sub-atmospheric pressure. The perfluorinated compounds fragment under these conditions prevailingly into difluoro carbenes :$CF_2$.

The so obtained hot "reaction mixture" is subsequently quenched, i.e., rapid cooling to below 400° C., generally below 300° C. and preferably below 100° C. typically within less than a second, preferably in less than 0.1 seconds. Cooling rates of $10^4$-$10^5$ K/sec may be used. These high cooling rates can be achieved either by conducting the hot reaction mixture through a bundle of pipes which are externally cooled or by injecting a coolant in the reaction mixture. The latter technology is also called wet quenching, the former dry quenching. Cold gases or liquids, like liquid perfluorinated carbons or water can be used as coolant. The efficiency of the quench process generally controls the selectivity of TFE. The higher the cooling rate the higher the selectivity and the less coking. Coking is formation of carbon arising via disproportionation of l$CF_2$ into carbon and $CF_4$. Coking interferes with the quench process.

Heating of the pyrolysis chamber can be achieved from external sources, like electric power or superheated steam. Typically, when using inductive heating the pyrolysis is carried out at a temperature of at least 500° C. to not more than 3000° C. A modern technology is inductive heating via microwaves. The needed powerful microwave generators are commercially available. Frequencies are usually at about 50 to 3000 kHz. Temperature is typically in the range of 600 to 3000° C., for example 700° C. to 2500° C. Inductive heating via microwaves is described in WO 95/21126, U.S. Pat. No. 5,110,996, WO 00/75092-A1, and WO 01/58584-A2.

Preferably, the pyrolysis proceeds in the presence of carbon. When inductive heating is used, carbon may be provided as a heat packing material. The use of carbon is particularly advantageous to convert $CF_4$, $C_2F_6$ and other perfluorinated compounds where the ratio fluorine atoms to carbon atoms is significantly greater than 2, e.g., greater than 2.5 or 2.7, to TFE. These compounds cannot be readily converted to TFE in absence of carbon because of stoichiometric constraints. The needed temperature to convert these perfluorinated compounds into TFE in the presence of carbon can be readily achieved with inductive heating.

Another method for pyrolysis is the Direct Current (DC) Plasma technology as described for example in U.S. Pat. No. 5,611,896 incorporated by reference herein. A carrier gas is needed to maintain the flame between the electrodes. Flame temperature may exceed 1000° K. Preferably, the DC plasma pyrolysis is also conducted in the presence of carbon. When $CF_4$ is a carrier gas, the $CF_4$ is also converted to TFE in addition to other perfluorinated compounds that have a lower fluorine to carbon ratio. Carbon may be provided for in the DC plasma pyrolysis through injection of powdery carbon or by operating "self consuming" carbon electrodes. The hot reaction mixture resulting in the DC plasma can be quenched as described above to obtain TFE and/or HFP at high selectivities. Plasma technology is, for example, covered in "Fluorine Reactions in Plasma" by Barry Bronfin, MIT PRESS, Mass. (1967). A further suitable DC plasma installation is described for example in WO 01/00156.

In a particular embodiment, pyrolysis at a temperature of not more than 3000° C., e.g., via inductive heating is used to pyrolyze perfluorinated compounds originating from the ECF effluent (e.g., FIG. 2, stream 12a) and a DC plasma is used to pyrolyze perfluorinated compounds originating from the ECF off-gas (e.g., stream 11c) and distillation (e.g., stream 30c). Preferably, each pyrolysis is conducted in the presence of carbon.

The process or part of it can be either batch or continuous. The ECF cell can produce a perfluorinated effluent that is fed batchwise to the pyrolysis, or the ECF cell can produce a perfluorinated effluent that is continuously fed into the pyrolysis. With either method, the process can be designed as a closed-loop.

Distillation

TFE and HFP are isolated from the quenched mixture of gases, (e.g., streams 20a and 40a FIGS. 1 and 2, via distillation (e.g., distillation 30, FIGS. 1 and 2). The mixture typically contains, TFE, HFP, perfluoroisobutylene (PFIB), and saturated perfluoroalkanes like $CF_4$, $C_2F_6$, or octafluorocyclobutane. In contrast to the commonly used "chlorine" process via R-22, hydrogen and chlorine containing chemical compounds are virtually absent. This renders the separation of TFE and HFP via distillation relatively simple in comparison to the R-22 process even when TFE is to be used in a subsequent polymerization to produce PTFE.

For making polymerization grade TFE, in particular for making PTFE, hydrogen and chlorine-containing monomers like vinylfluoride, vinylidene fluoride, trifluorochloroethylene and the like preferably are removed below the 1 ppm level because of their interference to make PTFE of desired quality and properties. Therefore, the existing processes require many distillation columns operated in complicated modes, as for example detailed in DE 37 29 106-A1. As a consequence, only units with a capacity of several 1000 tons TFE/year have been economically competitive.

The process of the present invention can yield polymerization grade TFE with only few distillation columns; essentially only 2 columns are needed to separate the "low boiling" components like $CF_4$, $C_2F_6$, cyc. $C_4F_8$ from the high boiling components like PFIB. The distillation cuts of these side products are fed back to pyrolysis (e.g., stream 30b, FIG. 1) to a low temperature pyrolysis using inductive heating, or in another embodiment of the present invention to a DC plasma furnace (e.g., DC plasma furnace 40 and stream 30c, FIG. 2).

Saturated perfluorinated components do not interfere at the polymerization and thus can be tolerated as contaminations even at higher concentrations. The same holds for saturated "perfluoro" chemical compounds containing "isolated" hydrogen atoms. Isolated hydrogen is understood as a single hydrogen flanked by C—F-bonds. These hydrogens virtually do not trigger chain transfer reactions at the polymerization. Thus, installation cost for the distillation are low. Smaller units with a capacity of less than 1000 tons TFE/year can thus be operated economically.

EXAMPLES

The following examples illustrate various specific features, advantages, and other details of the invention. The particular materials and amounts recited in these examples, as well as other conditions and details, should not be construed in a manner that would unduly limit the scope of this invention. All parts, percentages, and ratios are by weight unless otherwise specified.

Example 1

Simons Electrochemical Fluorination of Octane

A 1-liter electrochemical fluorination cell of the type described in U.S. Pat. No. 2,567,011, equipped with 2 overhead condensers having a nickel anode with a surface area of 0.037 $m^2$ was charged with 1000 grams $C_6F_{14}$, 40 grams of dimethyldisulfide, 40 grams of octane and 200 grams of anhydrous HF. The cell was operated at 45° C. and 2 bar. Voltage was between 5-6 Volts, current density about 1500 A/$m^2$. Voltage was reduced for 4 seconds to less than 4 Volts causing the current to fall to essentially zero after each 80 seconds ("intermitted current"). Octane was continuously fed to the cell to maintain its concentration in the circulating fluorochemical phase at about 5 wt %. Circulation rate was varied from 0.3 to 1 cell volume/hour with an external pump without an observably distinct effect on the fluorination rates.

The experiment was run for 500 hours. Intermittently, a portion of the fluorochemical phase was removed, the perfluoroalkanes were separated, partially stored and partially recycled back to the ECF cell. HF was replenished according to current consumption. The off-gas containing 1.7 volume % of fluorocarbons were stored in a vessel at 8 bar and subjected to the Membrane Process set forth in Example 2 below.

The perfluoroalkanes were analyzed via gas chromatography for perfluoro octane. The yield of which was 15 wt %. The other products are lower fluoroalkanes fragmented down up to $CF_4$. Current efficiency was about 95%.

Example 2

Membrane Process

The off-gas stream emanating from the ECF cell behind the overhead condensers at the run of Example 1 contained about 1.7 volume % of perfluorinated alkanes. Typical composition is shown in Table 1.

TABLE 1

Composition of off-gas; balance $H_2$

| | Components | | | | | | |
|---|---|---|---|---|---|---|---|
| | $CF_4$ | $C_2F_6$ | $C_3F_8$ | $C_4F_{10}$ | $C_3F_{12}$ | $CHF_3$ | Total |
| Volume % | 0.25 | 0.42 | 0.2 | 0.44 | 0.2 | 0.1 | 1.61 |

The off-gas stream was washed with aqueous NaOH solution, filtered to remove any liquid and solid particles compressed to 8 bar and fed to a 2-stage membrane system consisting of a polyimide, asymmetric composite hollow fiber membrane. A MEDAL™ Gas separation process from Air Liquide, Houston, Tex., according to Example 4 of U.S. Pat. No. 5,814,127 was used. The output of the $2^{nd}$ membrane module yielded 99.9% fluorocarbon with less than 0.1% $H_2$, the composition of which is given in Table 2. The "waste-stream" contained 99.7% hydrogen. The recovered fluorocarbons can be directly used as carrier gas at the DC plasma pyrolysis and also as feedstock for the inductive heating pyrolysis.

TABLE 2

Composition of the fluorocarbons separated from the ECF-off-gas

| | Components | | | | | | | |
|---|---|---|---|---|---|---|---|---|
| | $CF_4$ | $C_2F_6$ | $C_3F_8$ | $C_4F_{10}$ | $C_5F_{12}$ | $CHF_3$ | $H_2O$ | HF |
| Volume % | 16 | 26 | 12 | 27 | 12 | 6 | ~0.1 | <1 ppm |

Example 3

Preparation of TFE Via DC-Plasma Pyrolysis

A 30 kW DC plasma torch was used as described in WO 01/58841. Presence of carbon was given by "self-consuming" carbon electrodes. Dry quenching was used. The efficiency of this method is illustrated with pure fluorocarbons (Table 3) and the fluorocarbon mixture from the off-gas of Example 2 (Table 4). The carrier gas used was $CF_4$. The $CF_4$ stream was fed through a vaporizer containing the investigated fluorocarbons. Flow rate was varied from about 3.5 to 7.5 kg/hr. Results are shown in Table 3.

TABLE 3

DC plasma pyrolysis of selected fluorocarbons

| Perfluorinated Feed | Feed Rate kg/hr | | Flow Rate kg/hr of quenched reaction mixture | | | other |
|---|---|---|---|---|---|---|
| Stock* | Feed | $CF_4$ | $CF_4$ | $C_2F_4$ | $C_3F_6$ | FC's |
| $C_8F_{18}$ (FC 3225) | 0.45 | 3.0 | 1.7 | 1.2 | 0.15 | 0.4 |
| $C_7F_{16}$ (PF 5070) | 1.70 | 4.9 | 4.2 | 1.7 | 0.1 | 0.6 |
| $C_7F_{16}$ (PF 5070) | 1.53 | 3.0 | 2.4 | 1.3 | 0.0 | 0.8 |
| $C_6F_{14}$ (PF 5060) | 2.86 | 4.0 | 3.5 | 2.4 | 0.4 | 0.6 |
| $C_5F_{12}$ (PF 5050) | 4.40 | 3.0 | 3.7 | 3.7 | 0.0 | <0.1 |

*The Perfluorinated Feed Stock is available from 3M Company, St. Paul, MN.
HFP was produced with very low yields.

Table 4 gives the results of the fluorocarbon mixture as recovered from the off-gas (Example 2). No additional $CF_4$ was used as carrier gas.

TABLE 4

DC plasma pyrolysis of fluorocarbon mixture from off-gas

| Flow Rate kg/hr of off-gas | Flow Rate of quenched reaction mixture kg/hr | | | |
|---|---|---|---|---|
| fluorocarbons | $CF_4$ | $C_2F_4$ | $C_3F_6$ | Other FC's |
| 4.5 | 2.5 | 1.8 | 0.0 | 0.2 |
| 7.5 | 3.1 | 4.3 | 0.0 | 0.1 |

FC = fluorinated compound

Example 4

Preparation of TFE and HFP Via Inductive Heating Pyrolysis

A 10 kW installation as described in WO 01/58584-A2 was used. Frequency of microwaves was 800 kHz. Heat packing material used was graphite. Dry quenching was used. Perfluorooctane as model substance was investigated. It was fed in the installation in gaseous state via a vaporizer. Pressure was about 0.4 bar. Feed rate and average temperature was varied. Results are shown in Table 5.

TABLE 5

Pyrolysis of $C_8F_{18}$ via inductive heating

| | Temperature | | | |
|---|---|---|---|---|
| | 700° C. | | 1000° C. | |
| Flow Rate kg/hr of off-gas | Flow Rate of quenched reaction mixture kg/hr | | | |
| fluorocarbons | $C_2F_4$ | $C_3F_6$ | $C_2F_4$ | $C_3F_6$ |
| 2 | 1.3 | 0.5 | 1.0 | 0.3 |
| 5 | 2.5 | 0.8 | 2.1 | 0.6 |
| 10 | 3.0 | 0.8 | 1.9 | 0.4 |

Example 5

The same installation as in Example 4 was used to investigate the converting of $CF_4$ to TFE and HFP. Results are given in Table 6. $CF_4$ was fed into the installation at a flow-rate of 2 kg/hr at varying temperatures of the heating packing material (graphite). The same quenching as in Example 4 was practiced. Results are given in Table 6.

TABLE 6

Pyrolysis of $CF_4$; flow rate 2 kg/hr

| | Temperature ° C. | | | | |
|---|---|---|---|---|---|
| 900 | | 2000 | | 2500 | |
| | | Flow Rate kg/hr | | | |
| $C_2F_4$ | $C_3F_6$ | $C_2F_4$ | $C_3F_6$ | $C_2F_4$ | $C_3F_6$ |
| <0.1 | <0.1 | 0.5 | 0.2 | 0.7 | 0.2 |

Table 6 illustrates that $CF_4$ can be converted to TFE and HFP at reasonable rates. The yield for these monomers suffers from decreasing quenching rates at higher pyrolysis temperatures.

What is claimed is:

1. A process comprising:
   (a) perfluorinating a starting material comprising a linear or branched hydrocarbon compound, a partially fluorinated linear or branched hydrocarbon compound, or a mixture thereof by electrochemical fluorination (ECF) in an electrochemical cell (ECF cell) in a solution of anhydrous liquid hydrogen fluoride under temperature and pressure conditions sufficient to replace all hydrogens in at least part of the starting material with fluorine, to yield an ECF effluent wherein said ECF effluent comprises an off-gas and other ECF effluent constituents wherein the other ECF effluent constituents comprise perfluorinated and non-perfluorinated material;
   (b) separating the off-gas from the other ECF effluent constituents;
   (c) separating the other ECF effluent constituents to yield a perfluorinated feed material separated from the non-perfluorinated material;
   (d) pyrolyzing the perfluorinated feed material to yield a reaction mixture;
   (e) quenching the reaction mixture to yield a product mixture; and
   (f) recovering tetrafluoroethylene and/or hexafluoropropylene from said product mixture.

2. The process according to claim 1, wherein the starting material is a gas, a liquid, or a mixture thereof.

3. The process according to claim 1, wherein the starting material is selected from a group consisting of a straight or branched alkane of the formula: $C_nH_{2n+2}$, wherein n is from about 3 to about 25; an olefin; or combinations thereof.

4. The process according to claim 1, wherein the starting material is represented by the formula: $C_nH_xX_y$, wherein X is fluorine, and wherein x is at least 1 and x+y=2n+2.

5. The process according to claim 1, wherein the starting material is selected from a group consisting of butane, pentane, hexane, octane, and combinations thereof.

6. The process according to claim 1, wherein the starting material comprises a petroleum fraction having a boiling point of not more than 200° C.

7. The process according to claim 1 wherein said starting material is substantially free of one or more of chlorine, bromine and iodine containing materials.

8. The process according to claim 1, wherein the ECF process is selected from the group consisting of Simons ECF, interrupted current ECF, and bipolar flow cell ECF.

9. The process according to claim 1, wherein separating the other ECF effluent constituents comprises using simple distillation.

10. The process according to claim 1, wherein the perfluorinated feed material is pyrolyzed in the presence of carbon.

11. The process according to claim 1, wherein the pyrolysis is carried out using inductive heating at a temperature of not more than 3000° C.

12. A process comprising:
   (a) perfluorinating a starting material consisting essentially of a linear or branched hydrocarbon compound, a partially fluorinated linear or branched hydrocarbon compound, or a mixture thereof by electrochemical fluorination (ECF) in an electrochemical cell (ECF cell) in a solution of anhydrous liquid hydrogen fluoride under temperature and pressure conditions sufficient to replace all hydrogens in at least part of the starting material with fluorine, to yield an ECF effluent wherein said ECF effluent comprises an off-gas and other ECF effluent constituents wherein the other ECF effluent constituents comprise perfluorinated and non-perfluorinated material;
   (b) separating the off-gas from the other ECF effluent constituents;
   (c) separating the other ECF effluent constituents to yield a perfluorinated feed material separated from the non-perfluorinated material;
   (d) pyrolyzing the perfluorinated feed material to yield a reaction mixture;
   (e) quenching the reaction mixture to yield a product mixture; and
   (f) recovering tetrafluoroethylene and/or hexafluoropropylene from said product mixture.

* * * * *

UNITED STATES PATENT AND TRADEMARK OFFICE
CERTIFICATE OF CORRECTION

PATENT NO.        : 7,250,540 B2                                             Page 1 of 1
APPLICATION NO.   : 11/170385
DATED             : July 31, 2007
INVENTOR(S)       : Gerald L. Bauer It is certified that error appears in the above-identified patent and that said Letters Patent is hereby corrected as shown below:

Column 10
Line 1, delete "1000°" and insert -- 10000° --, therefor.

Signed and Sealed this

Seventeenth Day of February, 2009

JOHN DOLL
*Acting Director of the United States Patent and Trademark Office*